United States Patent [19]

Weinshenker et al.

[11] 4,115,545
[45] Sep. 19, 1978

[54] PHARMACEUTICAL COMPOSITION CONTAINING PROSTADIENOIC ACID FOR REGULATING GASTRIC SECRETION

[75] Inventors: Ned M. Weinshenker, Sunnyvale, Calif.; Niels H. Anderson, Seattle, Wash.

[73] Assignee: Alza Corporation, Palo Alto, Calif.

[21] Appl. No.: 823,811

[22] Filed: Aug. 11, 1977

Related U.S. Application Data

[60] Division of Ser. No. 570,621, Apr. 23, 1975, Pat. No. 4,055,593, which is a continuation of Ser. No. 117,166, Feb. 19, 1971, abandoned.

[51] Int. Cl.$^2$ .................. A61K 31/22; A61K 31/19; A61L 9/04
[52] U.S. Cl. .................. 424/45; 424/314; 424/317
[58] Field of Search .................. 424/45, 317, 318

[56] References Cited

U.S. PATENT DOCUMENTS 4,014,989  3/1977  Zaffaroni .................. 424/45

Primary Examiner—Frederick E. Waddell
Attorney, Agent, or Firm—Paul L. Sabatine; Steven D. Goldby

[57] ABSTRACT

Novel alkyl diethers of prostaglandins of the formula;

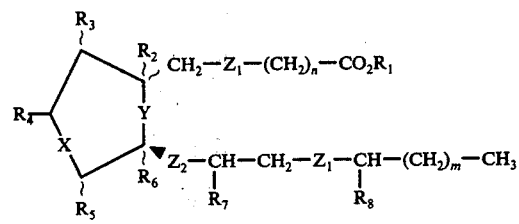

wherein $R_1$ is hydrogen or lower alkyl; $R_2$ and $R_6$ are hydrogen when Y is a single bond and $R_2$ and $R_6$ are absent when Y is a double bond; $R_3$ is keto,

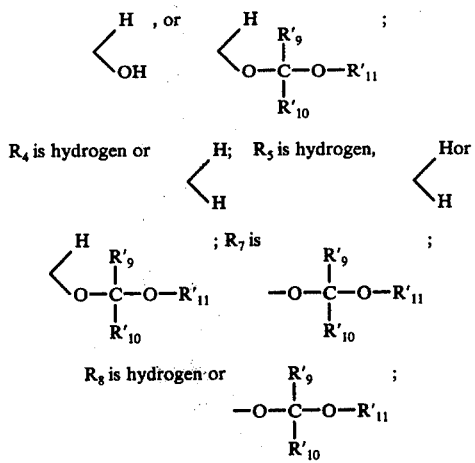

$R'_9$ is hydrogen or lower alkyl; $R'_{10}$ is lower alkyl; $R'_{11}$ is lower alkyl; $Z_1$ is cis or trans —CH=CH— or —CH$_2$CH$_2$—; $Z_2$ is trans —CH=CH— or —CH$_2$CH$_2$—; X is a single bond or a double bond and X is a single bond when $R_4$ and $R_5$ are hydrogen; Y is a single bond or a double bond; n is 1 to 5, m is 0 to 4; and the non-toxic salts. The prostaglandin ethers possess valuable pharmacological properties as modifiers of smooth muscle activity, gastric secretion, blood pressure, lipolysis and the reproductive system. The compounds also induce labor and menses and they can be used for the relief of asthma and nasal congestion. The compounds are also useful as platelet anti-clumping agents and for the inhibition of peptic ulcers.

2 Claims, No Drawings

PHARMACEUTICAL COMPOSITION CONTAINING PROSTADIENOIC ACID FOR REGULATING GASTRIC SECRETION

CROSS REFERENCE TO RELATED APPLICATIONS

This is a divisional application of application Ser. No. 570,621 filed Apr. 23, 1975, now U.S. Pat. No. 4,005,593, issued Oct. 25, 1977 which application is a continuation of application Ser. No. 117,166 filed Feb. 19, 1971, now abandoned.

BACKGROUND OF THE INVENTION

This invention relates to mono or di-substituted lower alkyl diether prostaglandins of Formula 1 as follows:

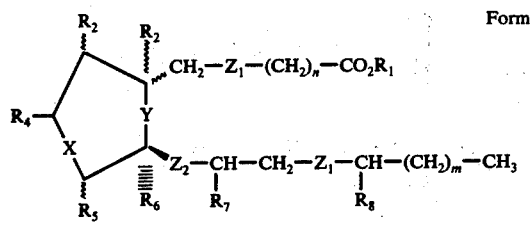

wherein:

$R_1$ is hydrogen or lower alkyl;

$R_2$ is hydrogen when $R_6$ is hydrogen and Y is a single bond, and $R_2$ is absent when $R_6$ is absent and Y is a double bond;

$R_3$ is keto group,

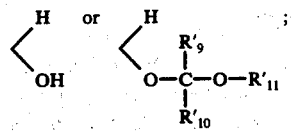

$R_4$ is hydrogen or

$R_5$ is hydrogen,

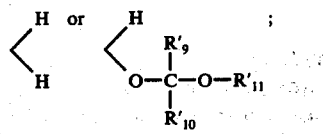

$R_7$ is

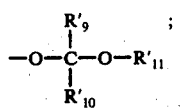

$R_8$ is hydrogen or

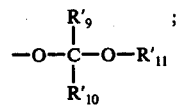

$R'_9$ is hydrogen or lower alkyl;
$R'_{10}$ is lower alkyl;
$R'_{11}$ is lower alkyl;
$Z_1$ is an unsaturated carbon carbon cis or trans —CH=CH—; or a saturated —$CH_2CH_2$— group;
$Z_2$ is an unsaturated carbon carbon trans —CH=CH—; or a saturated —$CH_2CH_2$— group;
X is a carbon carbon covalent bond or it is a carbon carbon covalent double bond with the proviso as set forth for $R_4$ and $R_5$ above;
Y is a carbon carbon covalent bond or it is a carbon carbon double bond with the proviso as set forth for $R_2$ and $R_6$ above;
n is 1 to 5 and m is 0 to 4; and the non-toxic salts thereof.

The term lower alkyl appearing above and elsewhere in the specification and claims denotes the straight and branched chain lower alkyl hydrocarbon groups of 1 to 8 carbon atoms inclusive, such as methyl, ethyl, n-propyl, iso-propyl, n-butyl, sec-butyl, pentyl, neopentyl, n-hexyl, isohexyl, heptyl and the like.

The term lower alkoxy appearing in the instant specification denotes straight and branched chain lower alkoxy hydrocarbon groups of 1 to 8 carbon atoms inclusive, such as methoxy, ethoxy, n-propoxy, butoxy, sec-butoxy, amoxy, iso-amoxy, hexyoxy, iso-butoxy, iso-propoxy, and the like.

The phrases pharmaceutically acceptable and non-toxic salts as embraced by the above Formulae and elsewhere in the disclosure and the accompanying claims includes the non-toxic alkali metal and the non-toxic alkaline earth metal bases such as sodium, potassium, copper, magnesium and the like, the hydroxides and carbonates thereof, the ammonium salts and substituted ammonium salts, for example, the non-toxic salts of trialkylamines such as triethylamine, trimethylamine and tri-isopropylamine, and other amines such as morpholine, diethylamine, dimethylamine, methylcyclohexylamine, glucosamine, procaine, dibenzylamine, triethanolamine, N-benzyl-β-phenylethylamine, ethyldimethylamine, benzylamine, N-(lower) alkyl piperidines, such as N-ethylpiperidine, N-methylpiperidine and other pharmaceutically acceptable amines. Also, non-toxic salts with monoalkyl and dialkylamines, and aralkylamines salts formed with compounds of Formula 1 ($R_1$=H) and tetra-alkylammonium hydroxides. The latter are generally called therapeutically acceptable quaternary ammonium salts, for example, tetramethylammonium, tetrapropylammonium, tetra-ethylammonium, phenyltriethylammonium, benzyltri-isopropylammonium salts, and the like.

The term "lower alkyl diether" as used herein denotes a lower alkyl substituted ether group of the formula

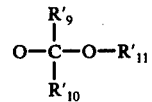

as covalently bonded to the prostaglandin backbone. The lower alkyl diether group is attached to the prostaglandin through an ether-carbon structure

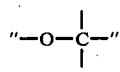

that may be conveniently named "methyloxy". The methyloxy group has bonded thereto the groups $R'_9$, $R'_{10}$ and $R'_{11}$. The group $R'_9$ is a hydrogen or lower alkyl group and $R'_{10}$ and $R'_{11}$ are lower alkyl groups. When $R'_9$, $R'_{10}$ and $R'_{11}$ are lower alkyl groups they may be the same or they may be different lower alkyl groups of the straight or branched chain hydrocarbon type of 1 to 8 carbon atoms inclusive, as defined above. The group $R'_{11}$ as bonded through the oxygen atom to the carbon atom may also be viewed as a lower alkoxy group. The lower alkoxy group, also an ether, is a straight or branched alkoxy group of 1 to 8 carbon atoms inclusive, as set forth above. Representative of diethers suitable for the present purpose are thus mono or lower dialkyl, lower alkoxy methyloxy groups such as (methyl' methoxy' methyloxy); (methyl' ethyl' methoxy' methyloxy); (ethyl' methyl' propoxy' methyloxy); (diethyl' methoxy' methyloxy); (ethyl' propyl' ethoxy' methyloxy); (dipropyl' ethoxy' methyloxy); (ethyl' iso-propyl' ethoxy' methyloxy) and the like.

The numbering system and the stereochemical nomenclature used for the novel prostaglandin ethers of the invention is the art accepted numbering and nomenclature. That is, the cyclopentane ring of the prostanoic acid is numbered 8 through 12 inclusive, the carboxyl side chain attached to the cyclopentane ring at its 8 position and the alkyl side chain attached to the cyclopentane ring at its 8 position and the alkyl side chain attached to the cyclopentane at its 12 position. When longer or shorter side chains are used, the carboxyl position is numbered as 1 and the numbers increased or decreased throughout the compound to correspond to the length of the chains and the ring inclusive. The stereochemistry of the substituents on the 5-membered cyclopentane ring may be α-oriented or β-oriented as indicated by a wavy line; the dashed line indicates an α-orientation and the solid wedged line indicates a β-orientation. Alpha-substituents are oriented on the opposite side of the cyclopentane ring as the ω-terminal chain, and β-substituents are oriented in the opposite sense; that is, on the same side as the alkyl side chain. Also, in the formulae as illustrated herein the substituents at positions $R_3$, $R_4$, $R_5$, and the like, as graphically depicted by

and the like, indicate that both groups, for example, hydrogen and hydroxyl, are bonded to the carbon atom of the cyclopentane ring. The substituents attached to the alkyl side chain may have a sinister (S) or rectus (R) configuration which for these compounds in the projection shown, is the equivalent nomenclature of α and β respectively. The diether prostaglandins depicted in the specification and accompanying claims thus includes the analogues and all the diastereomers thereof, and in addition, the enantiomeric forms and such mixtures as are designated racemates. The numbering system and the stereochemistry nomenclature is disclosed and described in Progress In The Chemistry of Fats and Other Lipids, Vol. IX, Part 2, pages 233 to 236, 1968, Pergamon Press, New York, and in J. Lipid Research, Vol. 10, pages 316 to 319, 1969.

DESCRIPTION OF INVENTIVE EMBODIMENTS

The novel lower alkyl diethers of prostaglandins of Formula 1 can be prepared from the corresponding prostaglandins, natural or synthetic, or from prostaglandin intermediates by separately converting them to the appropriate prostaglandin diether by chemical means. The corresponding starting prostaglandins can be represented by Formula 2 or from the starting prostaglandin intermediates represented by Formula 3:

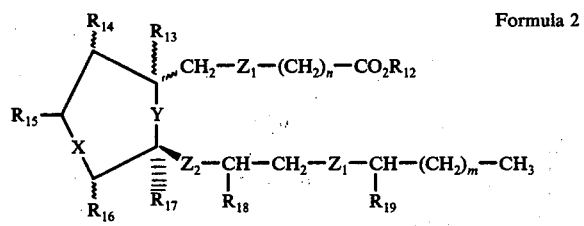

Formula 2

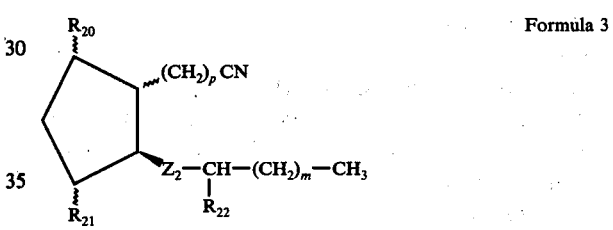

Formula 3 wherein Formula 2:

$R_{12}$ is hydrogen or lower alkyl;

$R_{13}$ is hydrogen when $R_{17}$ is hydrogen and Y is a single covalent bond and $R_{13}$ is absent when $R_{17}$ is absent and Y is a double covalent bond;

$R_{14}$ is a keto or

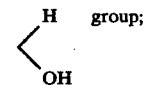

group;

$R_{15}$ is hydrogen or

$R_{16}$ is hydrogen,

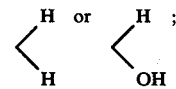

$R_{18}$ is a hydroxyl group;

$R_{19}$ is hydrogen or hydroxyl;

$Z_1$ is an unsaturated carbon carbon cis or trans group —CH=CH— or a saturated carbon carbon —CH$_2$CH$_2$—;

X is a carbon carbon single covalent bond or it is a carbon carbon double covalent bond and it is a double bond when $R_{15}$ and $R_{16}$ are hydrogen and a single bond when $R_{15}$ and $R_{16}$ are

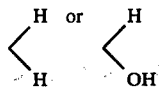

as above;

Y is a carbon carbon single covalent bond or it is a carbon carbon double covalent bond with the proviso as set forth for $R_{13}$ and $R_{17}$ above;

n is 1 to 5 and m is 0 to 4; and, wherein in Formula 3: $R_{20}$ is NHCHO, NHCOCH$_3$, NHCO-alkyl, or NH$_2$ $R_{21}$ is hydrogen,

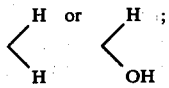

$R_{22}$ is hydroxyl;

p is 4 to 7 and m is 0 to 4, and the enantiomeric forms.

The starting prostaglandin materials of Formulae 2 and 3 used to synthesize the novel diether prostaglandins of Formula 1 are well known to the art and they are prepared by art known biosynthetic or chemical synthetic ways, or they are obtained from commercial sources. The starting materials of Formula 2 are prepared by the biosynthetic method of isolating the prostaglandin from natural sources, for example, the vesicular glands of sheep, or by the enzymatic conversion from fatty acid substrates, such as arachidonic acid, and, depending on the substituent desired, routinely chemically transforming double bonds to single bonds by hydrogenation, converting keto groups to hydroxymethylene groups by reduction, by dehydrating to introduce double bonds, by forming carbinol derivatives by treating carbo (lower) alkoxy groups with an alkali metal alumino hydride reducing agent such as lithium aluminum hydride and the like. The prior art methods that describe the procedures for providing all of the naturally derived starting compounds embraced by Formula 2 are found in Science, Vol 158, pages 382 to 391, 1967; Recueil, Vol 85, pages 1233 to 1250, 1966; Biochem. Biophysic. Acta., Vol 106, pages 215 to 217, 1965; Agnew. Chem. Inter. Ed., Vol 4, pages 410 to 416, 1965; Experientia, Vol 21, pages 113 to 176, 1965; Recueil, Vol 85, pages 1251 to 1253; and in other art recorded procedures.

The starting prostaglandin reactants and the starting intermediate prostaglandin reactants of Formula 2 and 3 can be chemically synthesized by well known procedures. For example, the prostaglandins can be synthesized from a common chemical intermediate 11,15-bis(-tetrahydropyranyl)ether of 9α,11α,15(S)-trihydroxy-5-cis,13-trans-prostadienoic acid according to the procedure reported in J. Am. Chem. Soc., Vol 92, pages 2586 to 2587, 1970, and references cited therein, to give the starting prostaglandins. The starting prostaglandins can also be prepared by the reduction of 2-oxa-3-oxo-6-exo-(trans-3-(S)-hydroxy-hept-1-enyl)-endo-7-acetoxy-cis-bicyclo(3.3.0)octane followed by reduction and treatment with Wittig reagent to give the corresponding prostaglandins as set forth in J. Am. Chem. Soc., Vol 91, pages 5675 to 5677, 1969; by the total synthesis of prostaglandins via a tricarbocyclic intermediate as reported in Tetrahedron Letters, Vol 4, pages 307 to 310, 1970; by the total synthesis of prostaglandins from 2-oxabicyclo(3.3.0)oct-6-en-3-one, ibid, pages 310 to 311, 1970; and other reported chemical synthesis embracing the prostaglandin materials within Formulae 2 and 3 such as the J. Am. Chem. Soc., Vol 90, pages 3245 to 3247, 1968; ibid, Vol 91, pages 535 to 536, 1969; ibid, Vol 92, pages 397 to 398, 1970; and in The Proceedings of the Robert A. Welch Foundation Conference on Chemical Research, Vol XII, pages 51 to 79, 1969. The intermediate prostaglandin starting materials as embraced by Formula 3 can also be prepared by the chemical synthetic route described in J. Am. Chem. Soc., Vol 90, pages 3245 to 3247, 1968; and ibid, pages 3247 to 3248, 1968; ibid, Vol 91, pages 535 to 536, 1969.

The novel diether prostaglandins of Formula 1 are prepared from the starting reactants represented by Formulae 2 and 3 by contacting and reacting the reactants of Formulae 2 and 3 generally under anhydrous conditions with an excess of an aliphatic enol ether; for example, with from about 1 to about 30 or more molecular equivalents of the aliphatic enol ether for each etherifiable hydroxyl group present in Formulae 2 and 3 to be etherified in the starting prostaglandin material. The reaction is carried out in an inert organic solvent and generally in the presence of a small amount of an acid catalyst. The reaction is usually carried out at a temperature of about 0° C. to about 80° C., usually at ambient temperature of about 25° C. The starting materials begin to react on contact but it is generally preferable to carry out the reaction for about 10 minutes to about 90 hours to produce from the starting reactants the corresponding ether compound of Formula 1.

The starting aliphatic enol ethers used for etherification of the various alcohol groups of the prostaglandin starting materials of Formula 2 and 3 to form the novel, improved alkali resistant, acid labile ethers prostaglandins of Formula 1 are obtained from commercial sources or they are readily prepared by the thermal decarboxylation of alkoxy unsaturated acids to yield the corresponding alkoxy enol ether according to J. Org. Chem., Vol 27, pages 3875 to 3878, 1962; and by the Claisen type reaction in Ber., Vol 31, pages 1019 to 1024, 1898. Exemplary of alkoxy enol ethers containing an olefinic group suitable for the purpose of the invention is methoxyisopropenyl ether, ethoxyisopropenyl ether, isopropoxyisopropenyl ether, n-butoxyisopropenyl ether, hexoxyisopropenyl ether, isobutoxy-isopropenyl ether and the like.

Exemplary of suitable inert, organic solvents for performing the etherification include anhydrous halogenated solvents such as methylene chloride, chloroform, carbon tetrachloride, ethylene chloride; anhydrous ether solvents such as diethylether, dimethylether; and other solvents such as anhydrous tetrahydrofuran, dioxane, n-hexane, cyclooctane, benzene, mixtures thereof, and the like. Representative of acid catalysts suitable for performing the reactions according to the spirit of the invention are p-toluenesulfonic acid, hydrochloric acid, anhydrous hydrobromic acid, Lewis acids such as boron trifluoride, boron trichloride etherate, stannic oxychloride, phosphorus oxychloride, phosphorus pentachloride, zinc chloride, mixtures thereof, and the like.

The novel diethers of prostaglandins can be chemically transformed to their non-toxic, pharmaceutically acceptable salt by neutralizing the prostaglandin diether with an equivalent or an excess amount of the corresponding non-toxic salt forming organic or inorganic base. The pharmaceutical salts are prepared by procedures known to the art, for example, equivalent or stoichiometric quantities of the prostaglandin and the organic base are dissolved in an inert organic solvent at room temperature or in a warmed solvent with a gentle mixing of the reactants, the prostaglandin diether and the base, until all the reactants are in solution. The product, or salt, is obtained by chilling the resulting mixture to precipitate the powder or crystals, or the product can be isolated by the addition of a miscible diluent of low polarity, or by the use of standard evaporation techniques. The inorganic prostaglandin diether salts are synthesized by procedures known to the art; for example, the prostaglandin diether is dissolved or dispersed in a mutual solvent containing stoichiometric amounts or an excess amount of a non-toxic salt forming inorganic compound. The synthesis can be carried out in the presence of an inert organic solvent and the product is obtained by procedures such as the evaporation of the reaction solvent, or by the addition of miscible solvents of low polarity, or by chilling the mixture to precipitate the product.

The lower alkyl esters of the prostaglandin diethers are obtained by known procedures, such as, the treatment of the diether of prostaglandin acid with a solution containing di(lower) azoalkanes to produce the corresponding diether prostaglandin ester. Esterification of the starting diether prostaglandin acid is performed by reacting the acid with the diazoalkane, for example, diazomethane, diazoethane, diazopropane, diazobutane, etc., in an inert organic solvent, for example, lower alkanols, symmetrical and unsymmetrical ethers, halogenated solvents, and other solvents such as tetrahydrofuran, acetone, dioxane, etc., or with mixtures thereof. The esterification reaction is usually performed at a temperature of 0° to 75° C., usually at ambient temperature and atmospheric pressure, with the ester recovered by evaporation of the solvent and by like techniques. Esterification reactions are described in Organic Chemistry, by Fieser and Fieser, pages 180 to 181, 1944.

The following examples are set forth as representative methods illustrative of the spirit of the present invention. These examples are not to be construed as limiting the scope of the invention as other functionally equivalent means will be readily apparent to those skilled in the subject art in the light of the present specification and accompanying claims.

EXAMPLE 1

Synthesis of 11,15-bis(dimethyl' methoxy' methyloxy)-13-trans prostenoic acid, (11,15-bis diether of $PGF_{2\alpha}$). Finely powdered 5-triphenylphosphonio pentanoic acid, 1.20 m mol is heated to 75° C. in vacuo for 1 hr and is then placed under an argon atmosphere. Dry dimethyl sulfoxide, 0.8 ml, is added to dissolve the warm solid and the resulting solution is cooled to ambient temperature. Then, 2.30 m mol of 2 M sodio methylsulfinylcarbonide, in dimethyl sulfoxide is added with stirring. Crude hemi acetal, Formula 4, 0.48 m mol,

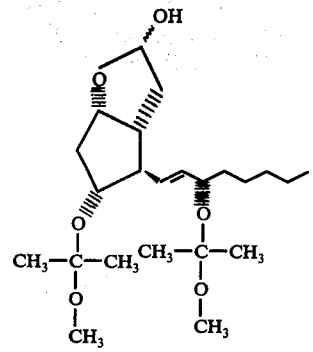

Formula 4 in 0.50 ml of dry dimethyl sulfoxide is added after 5 minutes. The mixture is stirred at ambient temperature for 1.0 hr, the dimethyl sulfoxide is removed under pressure (0.1 mm) and the residue is diluted with distilled water. The pH of the aqueous phase is adjusted to 9–10 with potassium carbonate. The neutral components are extracted with ethylacetate:ether (1:1) and then the aqueous phase is acidified with oxalic acid to pH about 3. Extraction with 1:1 pentane:ether is followed by washing the extracts with saturated brine and then drying over anhydrous magnesium sulfate. Concentration yields the desired product 11,15-bis diether of $PGF_{2\alpha}$.

EXAMPLE 2

Synthesis of 11,15-bis(dimethyl' methoxy' methyloxy)-9-oxo-5-cis,13-trans-prostadienoic acid,(11,15-bis diether of $PGE_2$). A mixture of the crude 11,15-bis diether of $PGF_{2\alpha}$ (as prepared above), 0.135 m mol, and 1.34 ml of acetone is cooled to −10° C. Then 59 μl (0.145 m mol) of Jones' Reagent is added over 5 minutes with stirring. After an additional 25 minutes at −10° C., isopropyl alcohol, 59 μl is added and after 5 minutes the mixture is diluted with 10 ml of ethyl acetate. The organic phase is separated, washed with water and saturated brine, dried over magnesium sulfate and concentrated to yield the 11,15-bis diether of $PGE_2$.

EXAMPLE 3

Synthesis of 11,15-bis(dimethyl' methoxy' methyloxy)-13-trans-prostenoic acid,(11,15-bis diether of $PGF_{1\alpha}$). A mixture of 0.076 m mol of 11,15-bis diether of $PGF_{2\alpha}$ (as prepared in Example 1) and 9.6 mg of 5% Pd/C in 5.0 ml of methanol is hydrogenated at −15° to −20° C. at atmospheric pressure. After about 3 hours the mixture is filtered through Celite 545, a commercially available diatomaceous silica, and concentrated in vacuo to leave the desired product also containing small amounts of 13,14-dihydro-bis diether of $PGF_{1\alpha}$.

EXAMPLE 4

Synthesis of 11,15-bis(dimethyl' methoxy' methyloxy)-9-oxo-13-trans-prostenoic acid,(11,15-bis diether of $PGE_1$). To a solution, cooled to −10° C., of $PGF_{1\alpha}$ (prepared in Example 3) in 1.48 ml of acetone is added 59.5 μl (0.148 m mol) of Jones Reagent After stirring for 5 minutes at −10° C., 59.5 μl of isopropyl alcohol is added and stirring is continued for 5 minutes at −10° C. After dilution with ethyl acetate the organic phase is washed with water and saturated brine, dried over anhydrous magnesium sulfate and concentrated to yield the desired product.

EXAMPLE 5

To a solution of 50 mg of 9α,11α,15(S)-trihydroxy-13-transprostenoic acid, (PGF$_{1\alpha}$), in 10 ml of anhydrous dioxane there is added 10 ml, an excess of ethoxyisopropenyl ether, CH$_3$C(OC$_2$H$_5$)=CH$_2$, boiling point 59°–62° C., and the solution is continually stirred to ensure a uniform mixture of the ingredients. To this mixture is next added about 5 mg of the acid catalyst, anhydrous p-toluenesulfonic acid, and the resulting reaction mixture is maintained with gentle stirring at ambient temperature for 72 hours. Next, the reaction mixture is washed with an aqueous 5% sodium carbonate and then with aliquots of water until a neutral pH is obtained for the mixture. The mixture is then dried over anhydrous sodium sulfate and evaporated to dryness. The dry residue obtained is dissolved in benzene-ethyl acetate and it is chromatographed through a column of neutral alumina to give 9α,11α,15(S)-tris(dimethyl' ethoxy' methyloxy)-13-trans-prostenoic acid.

EXAMPLE 6

Repeating the procedure of Example 5 but replacing 9α,11α,15(S)-trihydroxy-13-trans-prostenoic acid with:
9β,11α,15(S)-trihydroxy-13-trans-prostenoic acid, and,
9β,11α,15(S)-trihydroxy-5-cis,13-trans-prostadienoic acid,
9β,11β,15(R)-trihydroxy-13-trans-prostenoic acid,
racemic 9β,11β,15(R)-trihydroxy-5-cis,13-trans-prostadienoic acid,
9α,11α,15(S)-trihydroxy-5-cis,13-trans-prostadienoic acid, and,
9α,11α,15(S)-trihydroxy-5-cis,13-trans-17-cis-prostatrienoic acid, the following ethers are formed:
9β,11α,15(S)-tris-(dimethyl' ethoxy' methyloxy)-13-transprostenoic acid,
9β,11α,15(S)-tris(dimethyl' ethoxy' methyloxy)-9-cis,13-trans-prostadienoic acid,
9β,11β,15(R)-tris(dimethyl' ethoxy' methyloxy)-13-trans-prostenoic acid,
racemic 9β,11β,15(R)-tris(dimethyl' ethoxy' methyloxy)-5-cis,13-trans-prostadienoic acid,
9α,11α,15(S)-tris-(dimethyl' ethoxy' methyloxy)-5-cis,13-trans-prostadienoic acid, and,
9α,11α,15(S)-tris(dimethyl' ethoxy' methyloxy)-5-cis,13-trans, 17-cis-prostatrienoic acid.

EXAMPLE 7

To 50 mg of 15(S)-hydroxy-9-oxo-10,13-trans-prostadienoic and 20 ml of methylene chloride at 20° C, there is added an excess of 5 ml of methoxyisopropenyl ether CH$_3$C(OCH$_3$):CH$_2$, boiling point about 38° C., and 2 mg of anhydrous p-toluenesulfonic acid catalyst, and the mixture is gently shaken for about 15 to 20 minutes. Next, the reaction mixture is diluted with about 25 ml of ether containing 10 mg pyridine and washed with 10 ml aliquots of 50% brine and with 10 ml aliquots of saturated brine. Finally, the mixture is filtered, the residue is extracted with methylene chloride, freed of solvent and dried over anhydrous magnesium sulfate to give 15(S)-(dimethyl' methoxy' methyloxy)-9-oxo-10,13-trans-prostadienoic acid.

EXAMPLE 8

Repeating the procedure of Example 7 but substituting for 15(S)-hydroxy-9-oxo-10,13-trans-prostadienoic acid the following:

15(S)-hydroxy-9-oxo-5-cis,10,13-trans-prostatrienoic acid, and,
15(S),19-dihydroxy-9-oxo-10,13-trans-prostadienoic acid, the following ethers are obtained:
15(S)-(dimethyl' methyl' methyloxy)-9-oxo-5-cis,10,13-trans-prostatrienoic acid, and,
15(S),19-bis(dimethyl' methoxy' methyloxy)-9-oxo-10,13-trans-prostadienoic acid.

EXAMPLE 9

To a 250 ml roundbottom borosilicate flask containing 0.4 g of 15(S)-hydroxy-9-oxo-8(12),13-trans-prostadienoic acid in 15 ml of methylene chloride is added 5 ml of isopropoxyisopropenyl ether and 0.01 ml of phosphorus oxychloride and the flask's contents allowed to react at 20° C. for 36 hours. Next the reaction product is diluted with 25 ml of ether and washed with 50% brine and saturated brine until the solution is neutral. Next, the residue is extracted with methylene chloride, filtered, and freed of solvent under reduced pressure, dried over anhydrous magnesium sulfate, to give 15(S)-(dimethyl' isopropoxy' methyloxy)-9-oxo-8(12),13-trans-prostadienoic acid.

EXAMPLE 10

Following the procedure of Example 9, but replacing 15(S)-hydroxy-9-oxo-8(12),13-trans-prostadienoic acid with:
15(S)-hydroxy-9-oxo-5-cis,10,13-trans-prostatrienoic acid,
15(R)-9-oxo-10,13-trans-prostadienoic acid,
15(R)-hydroxy-9-oxo-5-cis,10,13-trans-prostatrienoic acid,
15(S),19-dihydroxy-9-oxo-10,13-trans-prostadienoic acid, the following diethers are formed:
15(S)-(dimethyl' isopropoxy' methyloxy)-9-oxo-5-cis,10,13-trans-prostatrienoic acid,
15(R)-(dimethyl' isopropoxy' methyloxy)-9-oxo-10,13-trans-prostadienoic acid,
15(R)-(dimethyl' isopropoxy' methyloxy)-9-oxo-5-cis,10,13-trans-prostatrienoic acid, and,
15(S),19-bis(dimethyl' isopropoxy' methyloxy)-9-oxo-10,13-trans-prostadienoic acid.

EXAMPLE 11

To a freshly prepared solution of 0.5 g of 9α,11α,15(S)-trihydroxy-13-trans-prostenoic acid in 30 ml of benzene is added 7.5 ml of butoxyisopropenyl ether and 0.01 g of anhydrous p-toluenesulfonic acid catalyst and the resulting mixture is allowed to stand at room temperature for about 48 hours. Following this reaction period, the mixture is washed with aliquots of 5% sodium carbonate solution and with distilled water until an essentially neutral pH is obtained for the aqueous phase. The mixture is then extracted with an organic solvent, dried over anhydrous sodium sulfate and then evaporated to dryness under in-house vacuum. The dry residue obtained is dissolved in hexane and chromatographed on a neutral alumina column to give 9α,11α,15(S)-tris(dimethyl' butoxy' methyloxy)-13-trans-prostenoic acid.

EXAMPLE 12

To 450 mg of 9-formamido,11α,15(S)-dihydroxy-13-trans-prostenonitrile, having the following structure, Formula 5,

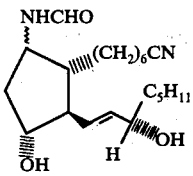

Formula 5 and prepared according to J. Am. Chem. Soc., Vol 90, pages 3245 to 3248, 1968, in 5 ml of methylene chloride there is added 5 ml of isopropyl isopropenyl ether, $CH_3C(OC_3H_8)=CH_2$, and 10 mg of anhydrous p-toluenesulfonic acid and the mixture shaken for 20 hours at ambient temperature. The reaction is quenched by the addition of pyridine and ether. The product is obtained from the ether solution after drying by evaporation of the solvent in vacuo. Next, the product 9-formamido,1-1α,15(S)-bis(dimethyl' isopropoxy' methyloxy)-13-trans-prostenonitrile, of the following structure, Formula 6,

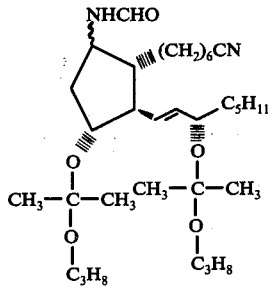

Formula 6 which is converted to the amino acid by the hydrolysis of the cyano group and deformylation with 4 chemical equivalents of KOH in MeOH—$H_2O$ at 110°-130° C for 16 hours in a sealed tube. The amino acid product is isolated by extraction with dichloromethane after addition of water and excess solid carbon dioxide. The amino group at the 9-position is next converted to its N-bromo derivative with N-bromosuccinimide in dichloromethane; then base catalyzed dehydrobromination, using alkoxides or amidines hydrolysis in dilute aqueous acetic acid and chromatography on silica to give 11α,15(S)-bis(dimethyl' isopropoxy' methyloxyl)-13-trans-prostenoic acid.

EXAMPLE 13

Following the procedure of Example 12, but replacing 9-formamido-11α,15(S)-dihydroxy-13-trans-prostenonitrile with:
  racemic 9-formamido-11β,15(S)-dihydroxy-13-trans-prostenonitrile,
  racemic 9-formamido-11α,15(R)-dihydroxy-13-trans-prostenonitrile,
  racemic 9-formamido-11β,15(R)-dihydroxy-13-trans-prostenonitrile, and
  enantio 9-formamido-11β,15(R)-dihydroxy-13-trans-prostenonitrile, also prepared by the method outlined in J. Am. Chem. Soc., Vol 90, pages 3245 to 3248, 1968; the following ethers are formed:
  racemic 11β,15(S)-bis(dimethyl' isopropoxy' methyloxy)-9-oxo-13-trans-prostenoic acid,
  racemic 11α, 15(R)-bis(dimethyl' isopropoxy' methyloxy)-9-oxo-13-trans-prostenoic acid,
  racemic 11β,15(R)-bis(dimethyl' isopropoxy' methyloxy)-9-oxo-13-trans-prostenoic acid, and,
  enantio 11β,15(R)-bis-(dimethyl' isopropoxy' methyloxy)-9-oxo-13-trans-prostenoic acid.

EXAMPLE 14

The compounds 9α-hydroxy,11α,15(S)-bis(lower dialkyl' methyloxy)-13-trans-prostenoic acid and 9β-hydroxy-11α,15(S)-bis(lower dialkyl' methoxy)-13-trans-prostenoic acid are prepared by the reduction of 11α,15(S)-bis(lower dialkyl' methyloxy)-9-oxo-13-trans-prostenoic acid using NaP $(R)_nH_{4-n}$ wherein R is a lower alkyl of 1 to 4 carbons in an inert organic solvent at 0° to 30° C. for 15 minutes to 1 hour to give the set forth prostaglandins. For example, the reduction is carried out using sodium borohydrie in methanol at 0° C. for 30 minutes followed by chromatographic separation to give the respective ether compounds.

EXAMPLES 15 to 18

The α-homo analogues of 11,15-bis(lower dialkyl' methyloxy)-5-cis,13-trans-prostadienoic acid,(11,15-bis ether of $PGF_{2α}$); of 11,15-bis(lower dialkyl' methyloxy)-9-oxo-5-cis,13-trans-prostadienoic acid,(11,15-bis ether of $PGE_2$); of 11,15-bis (lower dialkyl' methyloxy)-13-trans-prostenoic acid,(11,15-bis ether of $PGF_{1α}$); and of 11,15-bis(lower dialkyl' methyloxy)-9-oxo-13-trans-prostenoic acid,(11,15-bis ether of $PGE_1$) are prepared according to the procedure as set forth in Examples 1 to 4 inclusive, and all reaction conditions and reagents are as described except that 5-triphenylphosphonio hexanoic acid $\phi_3P^+CH_2(CH_2)_4-CO_2H\ Br^-$ ($\phi$=phenyl) is used in place of $\phi P^+CH_2(CH_2)_3CO_2H\ Br^-$ to give the desired compounds.

EXAMPLE 19

In this example, the 15-epimer of the lactone employed in Examples 15 to 18 inclusive, also prepared by the method set forth in J. Am. Chem. Soc., Vol 92, pages 2586 to 2587, 1970, and the references cited therein, and shown here as Formula 7, wherein R' is defined supra, and wherein

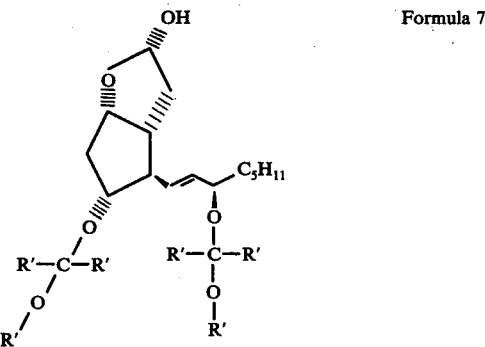

Formula 7 the hemiacetal is in either this form, or as the enantiomer is reacted with $\phi P^+CH_2(CH_2)_3CO_2H\ Br^-$ according to the method of Example 15 to 18 inclusive to produce the following ethers:
  11α,15(R)-bis(lower dialkyl' methyloxy)-9α-hydroxy-5-cis, 13-trans-prostadienoic acid,
  enantio 11α,15(R)-bis(lower dialkyl' methyloxy)-9α-hydroxy-5-cis,13-trans-prostadienoic acid,
  11α,15(R)-bis(lower dialkyl' methyloxy)-9-oxo-5-cis,13-trans-prostadienoic acid, and,
  enantio 11α,15(R)-bis(lower alkyl' methyloxy)-9-oxo-5-cis, 13-trans-prostadienoic acid.

EXAMPLE 20

Examples of additional(mono; or lower dialkyl' or alkoxy' methyloxy)-prostaglandins that are prepared in the mode and the manner of the present disclosure are as follows:

11α,15(S)-bis(methyl' methoxy' methyloxy)-9-oxo-5-cis,13-trans-prostadienoic acid, 11α,15(S)-bis-(ethyl' propoxy' methyloxy)-9-oxo-5-cis,13-trans,17-cis-prostatrienoic acid, 11α,15(S)-bis(ethyl' butyl' butoxy' methyloxy)-9-oxo-prostanoic acid, 11α,15(S)-bis(diethyl' butoxy' methyloxy)-9-oxo-13-trans-8-iso-prostenoic acid, 11α,15(S)-bis(dimethyl' isopropoxy' methyloxy)-9-oxo-13-transω-homo-prostenoic acid;

15(S)-(dipropyl' isopropoxy' methyloxy)-9-oxo-10,13-trans-prostadienoic acid,

15(S)-(isopropyl' methyl' isopropoxy' methyloxy)-9-oxo-5-cis, 10,13-trans-prostatrienoic acid, 9β,11α,15(S)-tris-(dibutyl' butoxy' methyloxy)-13-trans-prostenoic acid, 9α,11α,15(S)-tris(dibutyl' methoxy' methyloxy)-5-cis,13-trans-prostadienoic acid, 15(S)-(diamyl' isopropoxy' methyloxy)-9-oxo-8(12),13-trans-prostadienoic acid;

15(S),19-bis(diethyl' heptoxy' methyloxy)-9-oxo-10,13-trans-prostadienoic acid, and the like.

DESCRIPTION OF INVENTIVE APPLICATIONS

The novel prostaglandin ethers of the invention as embraced by Formula 1 possess valuable and useful properties. The prostaglandin ethers are inventively characterized by their ability to serve as a source of the parent prostaglandin following the metabolic hydrolysis of the prostaglandin from the diether moiety. For example, prostaglandin ethers with a C-9 keto group and one or both of the C-11 and C-15 positions substituted with a diether group on in vivo separation of the latter group and with the formation of hydroxyl groups make available prostaglandins that possess many pharmacological properties, including the ability to lower blood pressure and relieve asthma and nasal congestion. These parent prostaglandins are useful for the management of hypertension in avians, mammals, including humans and primates, farm animals and in laboratory animals. Also, following the liberation of the diether groups and with concomitant formation of hydroxyl groups in vivo, these will produce for example, 11α,15(S)-dihydroxy-9-oxo-5-cis,13-trans-prostadienoic acid; the latter compound when administered at the rate of 0.5 μg/min intravenously, or 2 mg/2 hrs intravaginally, or 0.5 mg/2 hrs orally, is known to be effective in humans for the induction of labor. Representative prostaglandin ethers for obtaining prostaglandins that possess the set forth pharmacological properties include 11α,15(S)-bis(lower alkyl' lower alkoxy', methyloxy)-9-oxo-13-trans-prostenoic acid; 11α,15(S)-bis(lower alkyl' lower alkoxy' methyloxy)-9-oxo-5-cis,13-trans-prostadienoic acid; 11α,15(S)-bis(lower alkyl' lower alkoxy' methyloxy)-9-oxo-5-cis,13-trans,17-cis-prostatrienoic acid, and the like.

The prostaglandin ethers of the invention substituted at the C-9, C-11 and C-15 positions with the diether group on liberation of the latter groups, and with concomitant in vivo formation of hydroxyl groups at the C-9, C-11 and C-15 positions, will produce prostaglandins possessing smooth muscle stimulating activity, for example, 9α,11α,15(S)-trihydroxy-13-trans-prostenoic acid; 9α,11α,15(S)-trihydroxy-5-cis,13-trans-prostadienoic acid, and the like, which latter compounds when administered intravenously (5 μg/min) or intravaginally (25 mg/2 hrs) will induce labor in humans. Exemplary of prostaglandin ethers that furnish corresponding prostaglandins which latter prostaglandins possess smooth muscle activity are 9α,11α,15(S)-tris(-lower alkyl' lower alkoxy' methyloxy)-13-trans-prostenoic acid; 9α,11α,15(S)-tris(lower alkyl' lower alkoxy' methyloxy)-5-cis,13-trans-prostadienoic acid; 9α,11α,15(S)-tris(lower alkyl' lower alkoxy' methyloxy)-5-cis,13-trans,17-cis-prostatrienoic acid; and the like.

The prostaglandin ethers of the invention that supply in vivo a physiologically active prostaglandin characterized by a C-9 keto group and (1) a C-11 and C-15 hydroxyl group or (2) a C-9, C-11 and C-15 hydroxyl group are physiologically useful for not only inducing labor but also menses and for the termination of pregnancy. Representative of prostaglandin ethers that can serve as an in vivo source of physiologically active prostaglandins when administered for example intravenously at the rate of 0.1 to 1.0 μg/min, calculated as freed prostaglandins are ethers such as 9α,11α,15(S)-tris(lower alkyl' lower alkoxy' methyloxy)-13-trans-prostenoic acid; 9α,11α,15(S)-tris(lower alkyl' lower alkoxy' methyloxy)-5-cis,13-trans-prostadienoic acid; 9α,11α,15(S)-tris(lower alkyl' lower alkoxy' methyloxy)-5-cis,13-trans,17-cis-prostatrienoic acid; 11α,15(S)-bis(lower alkyl' lower alkoxy' methyloxy)-9-oxo-5-cis,13-trans-prostadienoic acid; 11α,15(S)-bis(lower alkyl' lower alkoxy' methyloxy)-9-oxo-13-trans-prostenoic acid; and the like.

The prostaglandin ethers can be used for the relief of asthma, nasal congestion and inhibition of lipolysis by supplying from prostaglandin ethers substituted with a C-9 keto and a C-15 lower diether group or a prostaglandin ether substituted with a C-9 keto and at C-11 and C-15 a diether group the corresponding parent prostaglandins possessing the desired therapeutic utility. Exemplary of prostaglandin ethers of the invention for producing the corresponding prostaglandins include 15(S)-(lower alkyl' lower alkoxy' methyloxy)-9-oxo-10,13-trans-prostadienoic acid; 15(S)-(lower alkyl' lower alkoxy' methyloxy)-5-cis,10,13-trans-prostatrienoic acid; 11α,15(S)-bis(lower alkyl' lower alkoxy' methyloxy)-9-oxo-5-cis,13-trans-prostadienoic acid; and the like.

The prostaglandin ethers of the invention substituted with a C-9 keto group and additionally with a C-15 or C-11 and C-15 diether group are useful for the management of gastric secretions. These prostaglandin ethers release the natural anti-secretory prostaglandin in the stomach upon the acidic hydrolysis of the prostaglandin ether to free the prostaglandin group of the prostaglandin ether from the affixed ether moiety. The prostaglandin ether's ability to release free prostaglandin under gastric-like environmental conditions is demonstrated by standard in vitro experiments using an artificial gastric juice consisting essentially of mineral acid, hydrochloric, at varying pH from 1 to 4.5 at 37° C. For example, 11α,15(S)-bis(dimethyl' isopropoxy' methyloxy)-9-oxo-5-cis,13-trans-prostadienoic acid releases 11α,15(S)-dihydroxy-9-oxo-5-cis,13-trans-prostadienoic acid at pH 2 to 4 and at 37° C. The immediately described prostaglandin ethers are therapeutically indicated for regulating gastric secretions, that is, hyperacidity, because as the pH of the stomach reaches 4.5 to 5 the hydrolysis of the prostaglandin ether is essentially decreased, and, as the prostaglandin ether passes from the stomach into the intestine, the unwanted increased intestine peristalsis or increased intestinal motility with the accompanying bowel actions following administration of the natural form of the prostaglandins in the intestine are essentially absent for the prostaglandin ethers of the invention.

The prostaglandin ether's ability to release prostaglandin is determined by standard laboratory techniques, for example, by adding small amounts, 10 micrograms, 50 micrograms, etc., of the prostaglandin ether to hydrogen ion environments at varying pH and then detecting the presence of freed prostaglandin by conventional muscle bioassay. For example, the addition of $9\alpha,11\alpha,15(S)$-tris(diamyl' isopropoxy' methyloxy)-5-cis,13-trans-prostadienoic acid, and for racemic $9\alpha,11\alpha,15(S)$-tris(diethyl' ethoxy' methyloxy)-5-cis,13-trans-prostadienoic acid to a hydrogen ion environment, hydrochloric acid, indicated by rat bioassay, for example, contraction of isolated rat uterine or gerbil colon strips, that from about pH 1 to 4.5, hydrolysis of the ether linkage occurs to release the corresponding prostaglandin.

The prostaglandin ethers of the invention possess desirable partition coefficients between aqueous and lipid phases and they are therefore adaptable for administering for their physiologica effects from drug delivery systems, such as intrauterine contraception devices, skin drug delivery bandages and the like, manufactured from naturally occurring and synthetic polymeric materials. This novel and useful property of the prostaglandin ethers make possible their diffusion at measurable controlled rates through polymeric materials such as polyvinylchloride, polyisoprene, polybutadiene, polyethylene, ethylene-vinyl acetate copolymer, collagen, polydimethylsiloxane, hydrophilic hydrogels of esters of acrylic and methacrylic acids, polyvinyl acetates, propylene-vinyl acetate copolymers and the like.

The novel compounds of the invention can be used by the pharmaceutical and the veterinary arts in a variety of pharmaceutical preparations or veterinary preparations. In these preparations, the new compounds are administrable in the form of tablets, pills, powders, capsules, injectables, solutions, suppositories, emulsions, dispersions, food premix and in other suitable forms. The pharmaceutical or veterinary preparation which contains the compound is conveniently admixed with a non-toxic pharmaceutical organic carrier or a non-toxic pharmaceutical inorganic carrier. Typical of pharmaceutically acceptable carriers, are for example, water, gelatine, lactose, starches, magnesium stearate, talc, vegetable oils, polyalkylene glycols, petroleum jelly and other conventionally employed pharmaceutically acceptable carrier. The pharmaceutical preparation may also contain non-toxic auxiliary substances such as emulsifying, preserving, wetting agents and the like, as for example sorbitan monolaurate, triethanolamine oleate, polyoxyethylene sorbitan monopalmityl, dioctyl sodium sulfosuccinate, and the like.

Exemplary of a typical method for preparing a tablet containing the active ingredient is to first suitably comminute the active ingredient with a diluent such as starch, sucrose, kaolin or the like to form a powder mixture. Next, the just prepared mixture can be granulated by wetting with a non-toxic binder such as a solution of gelatin, acacia mucilage, corn syrup and the like and after mixing the composition is screened to any predetermined particle sieve size. As an alternative, if preferred to granulation, the just prepared mixture can be slugged through conventional tablet machines and the slugs comminuted before the fabrication of the tablets. The freshly prepared tablets can be coated or they can be left uncoated. Representative of suitable coatings are the non-toxic coatings including shellac, methylcellulose, carnauba wax, styrene-maleic acid copolymers and the like. For oral administration, compressed tablets containing 0.01 milligram, 5 milligrams, 25 milligrams, 50 milligrams, etc., up to 1500 milligrams are manufactured in the light of the above disclosure and by art known fabrication techniques well known to the art and set forth in *Remington's Pharmaceutical Science,* Chapter 39, Mack Publishing Co., 1965. The pharmaceutical manufacture of a formulation is shown in Example 21:

EXAMPLE 21

|  | Per Tablet, Mg |
|---|---|
| Prostaglandin ether | 2.0 |
| Corn Starch | 15.0 |
| Corn starch paste | 4.5 |
| Lactose | 82.0 |
| Calcium stearate | 2.0 |
| Dicalcium phosphate | 50.0 |

To formulate the tablet, uniformly blend the prostaglandin ether, corn starch, lactose, and dicalcium phosphate in a V-blender until all the ingredients are uniformly mixed together. Next, the corn starch is prepared as a 10% aqueous paste and it is blended with the uniform mixture until a uniform mixture is obtained. Then, the wet granulation is passed through a standard eight mesh screen, dried and rescreened with a twelve mesh screen. The dry granules are next blended with calcium stearate and compressed into tablets. Other tablets containing 0.05, 0.25, 1.0, 5.0, 10.0 mgs, etc. are prepared in a like fashion.

The manufacture of capsules containing 0.1 milligram to 1500 milligrams for oral use consists essentially of mixing the active compound with a non-toxic carrier and enclosing the mixture in a gelatin sheath. The capsules can be in the art known soft form of a capsule made by enclosing the compound in intimate dispersion within an edible oil or the capsule can be a hard capsule consisting essentially of the novel compound mixed with a non-toxic solid such as talc, calcium stearate, calcium carbonate or the like. Exemplary of a typical use employing capsules containing 25 mg of $11\alpha,15(S)$-bis-(lower dialkyl' lower alkoxy' methyloxy)-9-oxo-13-trans-prostenoic acid is therapeutically indicated ad libitum for regulating gastric secretions with lesser amounts indicated as the pH of the stomach reaches 4 to 5.

The daily dose administered for the compounds will of course vary with the particular novel prostaglandin ether employed because of the varying potency of the compounds, the chosen route of administration and the size of the recipient. The dosage administered is not subject to definite bounds, but it will usually be an effective amount or the equivalent on a molar basis of the pharmocologically active free acid form produced upon the metabolic release of the prostaglandin to achieve the biological function of the prostaglandin. Representative of a typical method for administering the diethers of prostaglandin of the invention is by the injectable-type administration route. By this route, a sterile solution containing the compound is administered intravenously or subcutaneously at the rate of 0.01 microgram to 0.50 microgram per kilogram of body weight per minute by means of an infusion pump at the rate of 10 to 15 milliliters per hour. For example, the compound 9α,1-1α,15(S)-tris(dimethyl' methoxy' methyloxy)-13-trans-prostenoic acid can be administered by this route for producing stimulation of smooth muscles. The compound is administered by the injectable route in a form suited for injection, such as mixed with sterile physiological saline, or in aqueous solutions having incorporated therein an agent that delays absorption such as aluminum monostearate and the like.

Suitable topical preparations can easily be prepared by, for example, mixing 500 mg of the diethers prostaglandins with 15 g of cetyl alcohol, 1 g of sodium lauryl sulfate, 40 g of liquid silicone D.C. 200 sold by Dow Corning Co., Midland, Michigan, 43 g of sterile water, 0.25 g of methylparaben and 0.15 g of propylparaben and warming the mixture with constant stirring to about 75° C. and then permitting the preparation to congeal. The preparation can be readily applied to the skin by inunction or it can be applied topically by dispensing the preparation from a conventional surgical gauze dispenser, and the like. The prostaglandin ethers penetrate the outermost layer of the skin, the stratum corneum, more readily than unetherified prostaglandins and as such the prostaglandin ethers lend themselves to topical administration. Suitable procedures for preparing topical applications are set forth in *Remington's Pharmaceutical Science*, Chapter 37, as cited supra.

The compounds of this invention can also be conveniently administered in aerosol dosage form. An aerosol form can be described as a self-contained sprayable product in which the propellant force is supplied by a liquified gas. For administering a self-propelled dosage form of about 25 mg to 150 mg that is used about 3 or 4 times daily for inhalation therapy, the bronchodialator 11α,15(S)-bis-(dimethyl' methoxy' methyloxy)-9-oxo-5-cis,13-trans-prostadienoic acid is suspended in an inert non-toxic propellant in a commercially available compressed-gas aerosol container. Suitable propellants include trichloromonofluoromethane, dichlorodifluoromethane, dichlorodifluoroethane, monochlorodifluoroethane and mixtures thereof. The inert gas can also be mixed with non-toxic cosolvents such as ethanol, if desired, to produce the aerosol form. If the compound is administered by oral inhalation employing conventional nebulizers, it is convenient to dilute in an aqueous solution about 1 part of the novel prostaglandin with about 1000 to 10,000 parts of solution, for administering 3 or 4 times per day.

For administering to valuable domestic household, sport or farm animals, such as sheep, goats, cattle, etc., or for administering to laboratory animals such as mice, rats, guinea pigs, monkeys, etc., for scientific studies, the compound is prepared in the form of a food premix, such as mixing with dried fish meal, oatmeal, straw, hay, ground corn, mash, and the like, and then the prepared premix is added to the regular feed, thereby administering the compound to the domestic or laboratory animal in the form of feed. The prostaglandin ethers can also be administered in laboratory studies for determining the therapeutic utility of the prostaglandin ethers to mammals, including humans, avains and other valuable animals by other well known methods. For example, in laboratory studies with standard white laboratory rats, the compounds can be administered orally by perfusion in saline at the rate of 0.1 microgram to 1.0 microgram per minute across the mucosal surface of the stomach to study muscle stimulation properties of the compounds.

The above examples and disclosure are set forth merely for illustrating the mode and the manner of the invention and various modifications and embodiments can be made by those skilled in the art in the light of the invention without departing from the spirit of the invention.

We claim:

1. A pharmaceutical composition useful for regulating gastric secretion in warm-blooded mammals, said composition comprising 0.1 milligram to 1500 milligrams of 11α,15(S)-bis(dimethyl',isopropoxy',methyloxy)-9-oxo-5-cis,13-trans-prostadienoic acid mixed with a therapeutically acceptable inert carrier stable in a warm-blooded mammal.

2. A pharmaceutical aerosol comprising 25 mgs to 150 mgs of 11α,15(S)-bis(dimethyl', isopropoxy', methyloxy)-9-oxo-5-cis,13-trans-prostadienoic acid suspended in a non-toxic, inert propellant, and wherein said aerosol is useful as a dosage sprayable bronchodilator.

* * * * *